(12) United States Patent
Toyoda

(10) Patent No.: US 11,175,247 B2
(45) Date of Patent: Nov. 16, 2021

(54) X-RAY IMAGING APPARATUS

(71) Applicant: Shimadzu Corporation, Kyoto (JP)

(72) Inventor: Toshihide Toyoda, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 138 days.

(21) Appl. No.: 16/668,630

(22) Filed: Oct. 30, 2019

(65) Prior Publication Data
US 2020/0064283 A1 Feb. 27, 2020

Related U.S. Application Data

(63) Continuation of application No. 15/741,380, filed as application No. PCT/JP2015/069462 on Jul. 6, 2015, now abandoned.

(51) Int. Cl.
| | | |
|---|---|---|
| *A61B 6/00* | (2006.01) | |
| *G01N 23/223* | (2006.01) | |
| *G01N 23/04* | (2018.01) | |
| *A61B 6/04* | (2006.01) | |
| *A61B 6/06* | (2006.01) | |

(52) U.S. Cl.
CPC .......... *G01N 23/223* (2013.01); *A61B 6/487* (2013.01); *A61B 6/5241* (2013.01); *A61B 6/544* (2013.01); *G01N 23/043* (2013.01); *A61B 6/0407* (2013.01); *A61B 6/06* (2013.01); *A61B 6/4435* (2013.01); *A61B 6/4452* (2013.01); *G01N 2223/612* (2013.01)

(58) Field of Classification Search
CPC .... G01N 23/223; G01N 23/04; G01N 23/043; G01N 23/02; G01N 23/06; G01N 23/083; G01N 23/00; G01N 2223/612; A61B 6/00; A61B 6/544; A61B 6/0407; A61B 6/5241; A61B 6/4435; A61B 6/487; A61B 6/486; A61B 6/405; A61B 6/54; A61B 6/542; A61B 6/5235; A61B 6/44; A61B 6/06; A61B 6/4452
See application file for complete search history.

(56) References Cited

FOREIGN PATENT DOCUMENTS

| | | |
|---|---|---|
| JP | 2011135990 | 7/2011 |
| JP | 2013192828 | 9/2013 |

OTHER PUBLICATIONS

JP 201580081315.6, First Office Action dated Mar. 31, 2020, 9 pages—English, 6 pages—Japanese.

*Primary Examiner* — Jurie Yun
(74) *Attorney, Agent, or Firm* — Andrew F. Young, Esq.; Nolte Lackenbach Siegel

(57) ABSTRACT

An X-ray imaging apparatus implements a fluoroscopy that irradiates a weaker dose of X-rays than a dose on the long-length imaging toward a subject M at each location in the long-length imaging range, while moving an X-ray tube in a body axis direction relative to the subject M prior to the long-length imaging, when the long-length imaging is implemented by moving the X-ray tube 2 in the body axis direction relative to the subject M. The dose $D_1$ at the location having the thick body thickness is less, so that the tube voltage is set up to be high as the tube voltage $V_1$ and vice versa, the dose $D_2$ at the location having the thin body thickness is high, so that the tube voltage is set up to be low as the tube voltage $V_2$.

1 Claim, 7 Drawing Sheets

X-RAY IMAGING APPARATUS

CROSS REFERENCE TO RELATED APPLICATIONS

This application relates to, and claims priority as a continuation of U.S. Ser. No. 15/741,380 filed Jan. 2, 2018, the entire contents of which are incorporated herein by reference, which in turn relates to and claims priority from Ser. No.: PCT/JP2015/069462 filed Jul. 6, 2015, the entire contents of which are incorporated herein by reference.

FIGURE SELECTED FOR PUBLICATION

FIGS. 5A, 5B

BACKGROUND OF THE INVENTION

Field of the Invention

The present invention relates to an X-ray imaging apparatus for X-ray imaging and particularly relates to the technology that generates a long-length image by connecting a plurality of X-ray images.

Description of the Related Art

Conventionally, relative to such device, a X-ray tube (X-ray radiation means) and a X-ray detector (X-ray detection means) moving along the direction of body axis of the subject are synchronously-operated so as to acquire X-ray images respectively and the acquired X-ray images are connected in the body axis direction to generate the long-length image. Particularly, the method for implementing long-length imaging to generate a long-length image by connecting X-ray images, which are acquired by squeezing the radiated visual field as like as a slit while adjusting the open-degree of the X-ray by a collimator, in the body axis direction (hereafter, "slot imaging") is disclosed.

With regard to a general long-length imaging including the slot imaging, the start position and the end position are set up in advance to specify the range of the long-length imaging (long-length imaging range). Therefore, the long-length imaging range is specified by setting up the start position and the end position by irradiating a light prior to the long-length imaging. However, when the light is irradiated, a body surface of a subject is only recognized, so that the location of organs and bones cannot be recognized. Now, the present applicant proposed the method to specify the long-length imaging range by setting the start position and the end position, for which an X-ray imaging prior to the long-length imaging is carried out and the X-ray image obtained thereby is displayed (e.g., Patent Document 1). According to such method, the location of the organs and the bones are recognizable by displaying the X-ray image that has been obtained in the past, so that the long-length imaging range can be specified highly accurately.

On the other hand, when the slot imaging is applied to acquire the long-length image of the large range of the entire spine or the entire lower leg, the fixed X-ray imaging condition (X-ray condition) is used to image. Such imaging condition may include a tube voltage, a tube electric current, and an irradiation time and so forth.

However, the imaging range (long-length imaging range) is large, so that the imaging condition may not be appropriate depending on the imaging location. Specifically, the X-ray may not transmit sufficiently or may transmit too much depending on the location, so that the generated long-length image (composite image) at the bottom line can be inappropriate for image-reading. Therefore, the method in which the imaging condition is gradated during a long-length imaging based on the predetermined setting can be proposed. However, even in such case, the body from the subject varies from a person to a person, so that it is supposed that such predetermined condition setting cannot provide a satisfactory result.

Now, the method, in which the X-ray imaging is implemented without a subject in advance, the predicted pixel value on long-length imaging is calculated, and the imaging condition of the long-length imaging is set up based on the obtained result, is disclosed (e.g., refer to the Patent Document 2). According to such method, when the long-length imaging is implemented using the set-up imaging condition, the long-length image (composite image) having a less visual connection portion can be obtained.

RELATED PRIOR ART DOCUMENTS

Patent Document

Patent Document 1-JP 2007-222500 A1
Patent Document 2-JP 2012-254160 A1

ASPECTS AND SUMMARY OF THE INVENTION

Objects to be Solved

However, even when the method disclosed in the Patent Document 2, JP 2012-254160 A1, illustrated above, is used, the data as to the body frame of the subject is not obtained in advance, so that it is problematic that the imaging condition for the long-length imaging cannot be set up accurately.

Considering such circumstances, the object of the present invention is to provide an X-ray imaging apparatus capable of appropriately setting an imaging condition for a long-length imaging that takes the different range of the height (body thickness) of the subject.

Means for Solving the Problem

The inventor of the present invention studied extensively to solve the above problem and found the following solutions.

Specifically, an X-ray imaging apparatus equips an automatic brightness control (IBS) function for the X-ray imaging other than the long-length imaging. Such imaging condition includes the tube voltage, the tube electric current, and the irradiation time and so forth. Specifically, a fluoroscopy is implemented with a weaker wave dose than the wave dose upon imaging prior to the X-ray imaging so that the imaging condition (e.g., the tube voltage) is set up to adjust the brightness (pixel value) based on the obtained fluoroscopic result. When the thick subject is subject to imaging, the X-ray dose that reaches to the X-ray detector (X-ray detection means) is less, so that the tube voltage is increased to prevent such incident, and vice versa, when the thin subject is subject to imaging, the X-ray dose that reaches to the X-ray detector (X-ray detection means) is higher, so that the tube voltage is decreased to prevent such incident. As results, even when the height (body thickness) of the subject is different, the X-ray dose that reaches to the X-ray detector (X-ray detection means) can be uniformed, so that the brightness (pixel value) can be appropriately adjusted.

On the other hand, the purpose of implementing the X-ray imaging prior to the long-length imaging is to specify the range of the long-length imaging (long-length imaging range) as disclosed in the Patent Document 1, JP2007-222500 A1 as set forth above. In addition, even when the method disclosed in the paragraph [0026] of the Patent Document 2, JP 2012-254160 A1 as illustrated above is described as "the calculation method calculates the radiation strength irradiated from the X-ray source is calculated using an inverse-square law, i.e., such strength is an inverse proportion of the distance, but the data as to the body frame of the subject is not obtained in advance as set forth above, so that the imaging condition for the long-length imaging cannot be set up accurately. Considering such circumstances, it is preferable that the data of the subject is obtained in advance even relative to the long-length imaging.

Now, the inventor notices that the automatic brightness control (IBS) function should be applied to the long-length imaging. In such way, the inventor found that as well as the long-length imaging, when the fluoroscopy is implemented while moving the X-ray tube (X-ray irradiation means) and the X-ray detector (X-ray detection means) in the body axis direction prior to the long-length imaging and the wave dose of the X-ray (that reaches to the X-ray detector) is obtained as the fluoroscopic result every location of each of the long-length imaging range and subsequently, the imaging condition is set up based on such X-ray dose (fluoroscopic result), the imaging condition can be appropriately set up relative to the long-length imaging that takes the different ranges with each other as to the height of the subject (body thickness). The X-ray dose at the location having the thick body thickness is less and the X-ray wave dose at the location having the thin body thickness is high. Specifically, the wave dose of the X-ray that reaches to the X-ray detector is the wave dose of the X-ray that transmits the subject and equivalent to the data as to the height of the subject.

Further, such function can be extended to the data as to the height of the subject other than the X-ray dose, and in addition, extended to the electromagnetic wave (e.g., light) and the ultrasound. In such way, the inventor found that as well as the long-length imaging, when the electromagnetic wave or the ultrasound is irradiated while moving the electromagnetic wave irradiation means or the ultrasound irradiation means in the body axis direction prior to the long-length imaging and when the data as to the height of the subject every location with each other relative to the long-length imaging range are obtained, and the imaging condition is set up based on such data; the imaging condition can be appropriately set up relative to the long-length imaging that takes the different ranges as to the height of the subject (body thickness).

The present invention based on such finding constitutes the following structure.

Specifically, an X-ray imaging apparatus of the present invention is an X-ray imaging apparatus that implements an X-ray imaging comprises; a data acquisition means that acquires a plurality of data relative to a height of a subject at each location relative to a long-length imaging range; an imaging condition setting means that sets up an X-ray imaging condition so that doses of X-rays that transmit the subject coincide with each other at each location based on data relative to the height of the subject at each location in the long-length imaging range that are acquired using the data acquisition means; an X-ray irradiation means that irradiates the X-ray to the subject based on the imaging condition that is set up by the imaging condition setting means; an X-ray detection means that detects the X-ray that transmits the subject; and an image connection means that connects a plurality of X-ray images acquired by the X-ray detection means to generate a long-length image The X-ray imaging apparatus according to the aspect of the present invention comprises a data acquisition means that acquires each of data as to a height of a subject every location relative to a long-length imaging range with each other. The X-ray imaging apparatus according to the aspect of the present invention further comprises an imaging condition setting means that sets up an X-ray imaging condition so that doses of X-rays that transmit the subject coincide with each other at each location based on data relative to the height of the subject at each location in the long-length imaging range that are acquired using the data acquisition means; The data acquisition means that acquires each of data as to a height of a subject every location relative to a long-length imaging range with each other prior to the long-length imaging. The imaging condition setting means that sets up an X-ray imaging condition so that doses of X-rays that transmit the subject coincide with each other at each location based on data relative to the height of the subject at each location in the long-length imaging range, and implements the long-length imaging, so that the imaging condition relative to the long-length imaging in the region in which the height (body thickness) of the subject is different each other can be set up appropriately.

According to the X-ray imaging apparatus of the present invention as set forth above, the above described data acquisition means comprises: an electromagnetic wave irradiation means that irradiates an electromagnetic wave to a subject so that the electromagnetic wave is incident into each location relative to the long-length imaging range set forth above; a data conversion means that converts each of data as to a height of a subject every location relative to a long-length imaging range with each other based on the electromagnetic wave irradiated from the electromagnetic wave irradiation means. The electromagnetic wave irradiation means irradiates the electromagnetic wave to the subject so that the electromagnetic wave is incident into each location relative to the long-length imaging range prior to the long-length imaging. The data conversion means converts the dose of the electromagnetic wave to the data relative to the height of the subject at each location in the long-length imaging range based on the electromagnetic wave that is irradiated from the electromagnetic wave irradiation means; and the imaging condition setting means sets up an X-ray imaging condition so that doses of X-rays that transmit the subject coincide with each other at each location based on data relative to the height of the subject at each location in the long-length imaging range, and implements the long-length imaging, so that the imaging condition relative to the long-length imaging in the region in which the height (body thickness) of the subject is different each other can be set up appropriately.

One example of the electromagnetic wave that is irradiated as set forth above (irradiated prior to the long-length imaging) is an X-ray. In such case, the fluoroscopy, in which a weaker dose of an X-ray than on the long-length imaging to generate the long-length image is irradiated to a subject from an electromagnetic wave irradiation means, is implemented at each and every location relative to the long-length imaging range, and based on the results of the fluoroscopy, the data conversion means converts the dose of the electromagnetic wave to the data related to the height of the subject at each and every location in the long-length imaging range. The fluoroscopy, in which a weaker dose of an X-ray than on the long-length imaging to generate the long-length image is irradiated to a subject from a electromagnetic wave irradiation means, is implemented at each and every location relative to the long-length imaging range prior to the long-length imaging. In such way, every time when the fluoroscopy is implemented at each location relative to the long-length imaging range, the data conversion means converts the transmitted X-ray dose to the data related to the height of the subject at each location in the long-length imaging range based on the results of the fluoroscopy prior to the long-length imaging. The imaging condition setting means that sets up an X-ray imaging condition so that doses of X-rays that transmit the subject coincide with each other at each location based on data relative to the height of the subject at each location in the long-length imaging range, and implements the long-length imaging, so that the imaging condition relative to the long-length imaging in the region in which the height (body thickness) of the subject is different each other can be set up appropriately.

When the electromagnetic wave is an X-ray, it is preferable that the X-ray irradiation means is the electromagnetic wave irradiation means as well. Accordingly, the number of the component parts of the apparatus can be cut.

In addition, when the electromagnetic wave is the X-ray, the data relative to the height of the subject at each location in the long-length imaging range is the dose of the X-ray that transmits the subject. When the automatic brightness control (IBS) function is equipped, the X-ray dose that reaches to the X-ray detector (X-ray detection means) is less, so that the tube voltage is increased to prevent such incident, and vice versa, when the thin subject is subject to imaging, the X-ray dose that reaches to the X-ray detector (X-ray detection means) is higher, so that the tube voltage is decreased to prevent such incident. As results, the X-ray dose that reaches to the X-ray detector (X-ray detection means) can be uniformed even when the height (body thickness) of the subject is different in the long-length imaging range, so that the brightness (pixel value) can be appropriately adjusted.

Effect of the Invention

According to the X-ray imaging apparatus of the present invention, the data acquisition means that acquires each of data as to a height of a subject every location relative to a long-length imaging range with each other prior to the long-length imaging. The imaging condition setting means that sets up an X-ray imaging condition so that doses of X-rays that transmit the subject coincide with each other at each location based on data relative to the height of the subject at each location in the long-length imaging range, and implements the long-length imaging, so that the imaging condition relative to the long-length imaging in the region in which the height (body thickness) of the subject is different each other can be set up appropriately.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Figure 1:
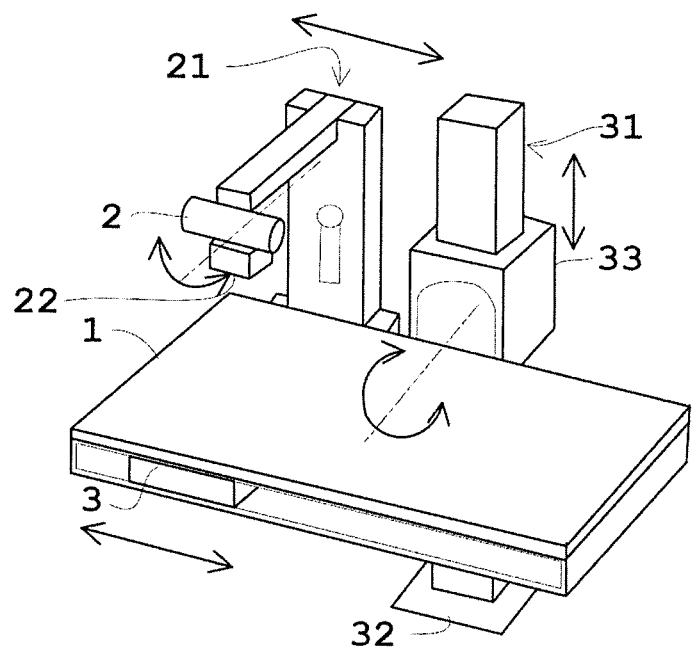
FIG. 1 is a schematic perspective view illustrating an X-ray imaging apparatus according to the aspect of the Embodiment.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

It will be further understood by those of skill in the art that the apparatus and devices and the elements herein, without limitation, and including the sub components such as operational structures, circuits, communication pathways, and related elements, control elements of all kinds, display circuits and display systems and elements, any necessary driving elements, inputs, sensors, detectors, memory elements, processors and any combinations of these structures etc. as will be understood by those of skill in the art as also being identified as or capable of operating the systems and devices and subcomponents noted herein and structures that accomplish the functions without restrictive language or label requirements since those of skill in the art are well versed in related X-Ray diagnostic devices, computer and operational controls and technologies of radiographic devices and all their sub components, including various circuits and combinations of circuits without departing from the scope and spirit of the present invention.

Figure 2:
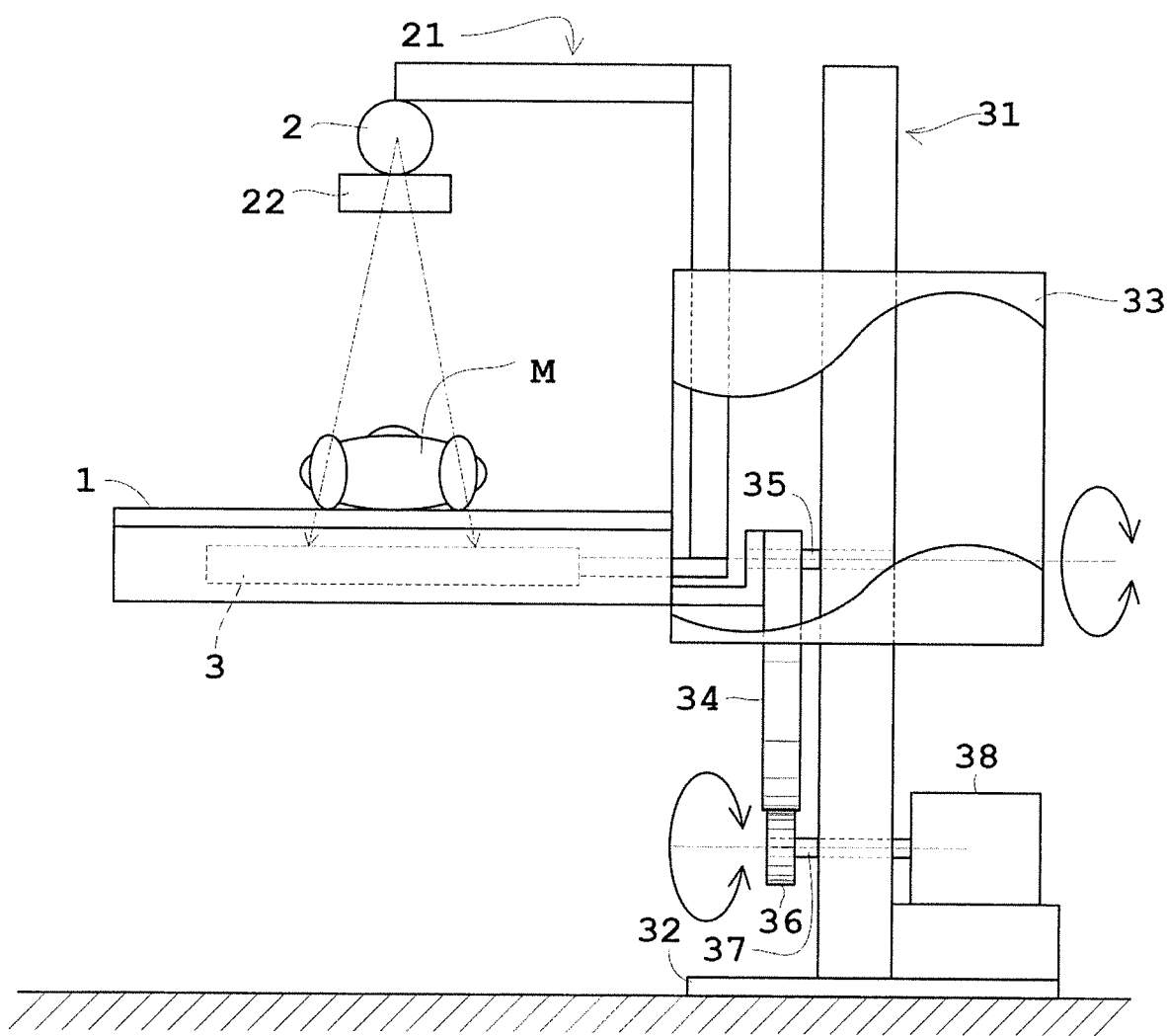
FIG. 2 is a schematic front view illustrating an X-ray imaging apparatus according to the aspect of the Embodiment.
Figure 3:
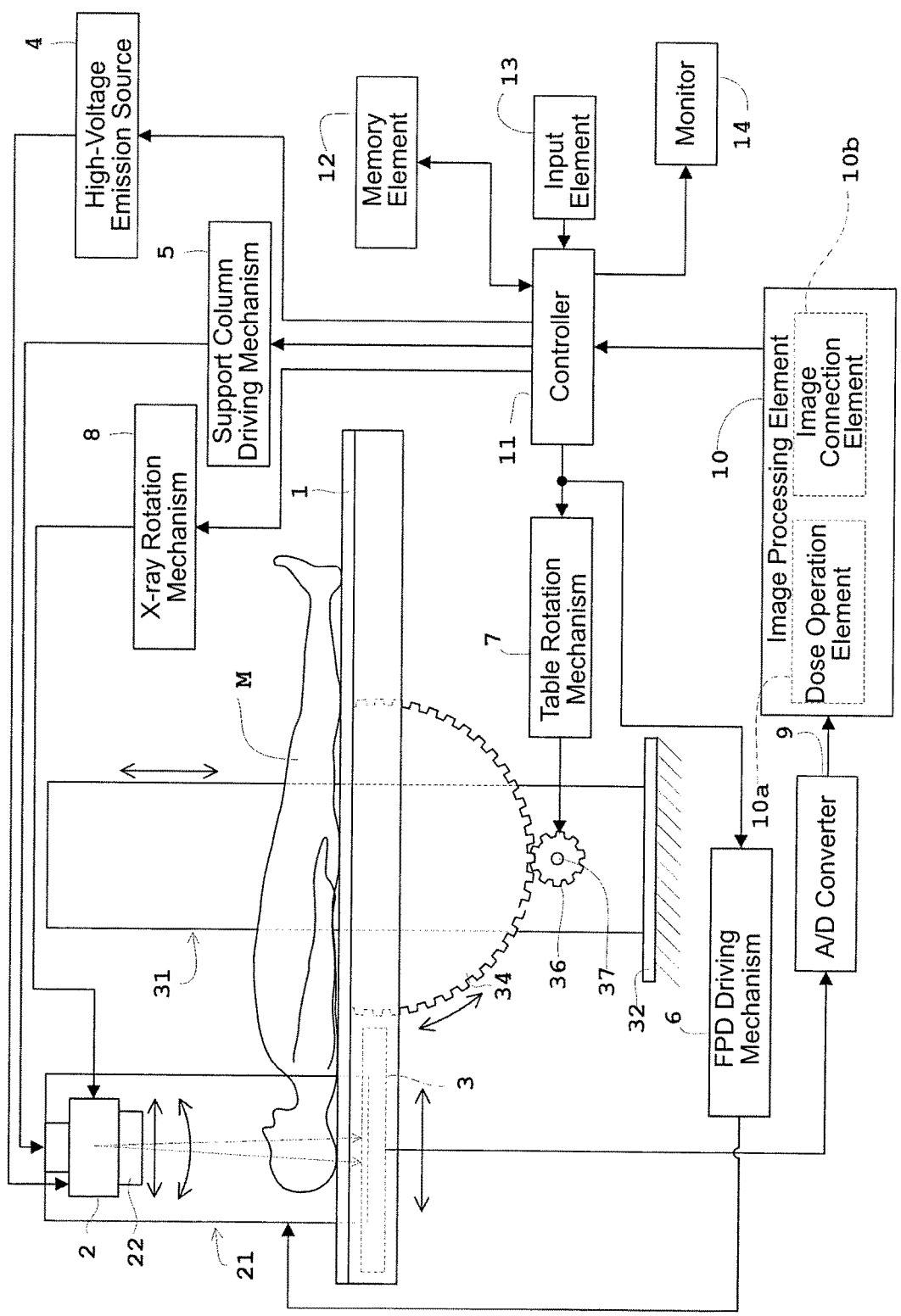
FIG. 3 is a schematic side view and a block diagram illustrating an X-ray imaging apparatus according to the aspect of the Embodiment.

Referring now to the Figures, the inventor sets forth the Embodiment of the present invention. FIG. 1 is a schematic perspective view illustrating an X-ray imaging apparatus of the Embodiment, FIG. 2 is a schematic front view illustrating an X-ray imaging apparatus of the Embodiment and FIG. 3 is a schematic side view and a block diagram illustrating an X-ray imaging apparatus of the Embodiment. A table supporting element and so forth are not shown in FIG. 3. According to the aspect of the Embodiment, the inventor sets forth an electromagnetic wave that is irradiated prior to a long-length imaging is an X-ray for example, and a dose of the X-ray that transmits a subject (X-ray after transmitting) as the data relative to the height of the subject for example.

Referring to FIGS. 1-3, an X-ray imaging apparatus comprises a table 1 on which a subject M is laid, an X-ray tube 2 to irradiate X-ray to the subject M and the flat panel type X-ray detector (FPD) 3 to detect the X-ray that transmits through the subject M. FPD 3 is installed inside the table 1. The X-ray tube 2 corresponds to the X-ray irradiation means of the present invention and the flat panel type detector (FPD) 3 corresponds to the X-ray detection means of the present invention. In addition, the X-ray tube 2 corresponds to the electromagnetic wave irradiation means of the present invention.

The X-ray imaging apparatus comprises a support column 21 to support the X-ray tube 2 and a main support column 31 to support the table 1. A collimator 22 that controls the bright visual field by adjusting the open-degree of the X-ray irradiated from the X-ray tube 2 is installed in the irradiation side of the X-ray tube 2. According to the aspect of the present Embodiment, one end of the support column 21 supports the X-ray tube 2 as described above and the other end supports the FPD 3 installed inside the table 1 so that the X-ray tube 2 and the FPD 3 move in the same direction with each other and parallel to the table 1 along the longitudinal direction of the subject M (refer to FIG. 3.) In addition, while the X-ray tube 2 and the FPD 3 are moving in the same direction with each other and parallel to the table 1 along the longitudinal direction of the subject M, the slit-like X-ray is irradiated from the X-ray tube 2 and the FPD 3 detects the X-ray to implement an X-ray imaging under the squeezed narrower condition (refer to FIG. 3) than the bright visual field projected on the FPD 3.

The main support column 31 is installed vertically on the base 32 installed on the floor surface, to which the table holding element 33 is mounted so as to be capable of up-and-down (tilting) the table 1. The main support column 31 is installed vertically on the base 32 installed on the floor surface and the table holding element 33 is installed to hold the table 1 so that the FPD 3 installed inside the table 1, the support column holding the FPD 3 at the other end, the X-ray tube 2 supported at the one end of the support column 21 and the collimator 22 installed in the irradiation side of the X-ray tube 2 can be supported.

The table holding element 33 comprises a fan-shaped rack 34 that rotates and tilts the table 1 around the center of axis of the horizontal axis, a spindle 35 inserted into the fan-shaped rack 34 and the main support column 31, a pinion 36 fit into the fan-shaped rack 34, a rotation shaft 37 having the pinion 36 at the one end thereof and a motor 38 that rotates the rotation shaft 37 therein. The motor 38 rotates the rotation shaft 37 so that the pinion, mounted to the one end of the rotation shaft 37, can rotate and then the fan-shaped rack 34 fit therein rotates, in interlock with the rotation of the pinion 36, around the spindle 35 as the spindle 35 is the fulcrum therefor. The fan-shaped rack 34 rotates around the spindle 35 so that the table 1 can be rotated and tilted around the center of axis of the horizontal axis.

In such way, when the table 1 rotates and tilts around the center of axis of the horizontal axis, the table 1 can take an upright posture, a tile posture and a horizontal posture (recumbent posture) by the up-and-down operation. In addition, the supporting column 21 tilts along with that the x-ray tube 2 the X-ray tube 2 and the FPD 3 tilts, in interlock with the tilt of the table 1. Further, when the table 1 is tilted into the upright posture and the distance from the rotation position around the center of axis of the horizontal axis to the lower region of the table 1 is longer than the height from the spindle 35 of the support column 31 to the lower region of the support column 31, the upright posture cannot be brought in reality, but in such case, if the table 1 is moved to the upper region, the upright posture can be brought in reality.

The X-ray imaging apparatus, referring to FIG. 3, comprises: a high-voltage generator 4 that generates tube voltages and tube electric current; a support column driving mechanism 5 that drives a motor (not shown in FIG.) to move the support column 21 along with the X-ray tube 2 and the collimator 22 which are supported thereby, parallel to the table 1 along the longitudinal direction, which is the body axis of the subject M; a FPD driving mechanism 6 that drives the motor (not shown in FIG.) to move the FPD 3 parallel to the table 1 along the longitudinal direction; a table rotation mechanism 7 that drives the motor 38 (refer to FIG. 2) to operate the table 1 described above up-and-down (tilting); an X-ray tube rotation mechanism 8 that drives the motor (not shown in FIG.) to rotationally move the X-ray tube 2 around the center of axis of the connected axis (i.e., axis orthogonal to the body axis); an A/D converter 9 to digitize and take out the X-ray detection signal, which is a charge signal, from the FPD 3; an image processing element 10 that executes a variety of processings based on the X-ray detection signal output from the A/D/ converter 9; a controller 11 that controls each element overall; a memory 12 in which the processed X-ray image and so forth are stored; a input element 13 on which the operator carries out the input-setting; a monitor 14 that displays the processed X-ray image and so forth; and so forth. The controller 11 corresponds to the imaging condition setting means of the present invention. The inventor sets forth a specific setting and operation of the controller 11 referring to FIG. 4, FIGS. 5A, 5B later.

The image processing element 10 comprises: a dose operation unit 10a that obtains the dose of the X-rays (X-ray after transmitting), which transmit the subject M at each location in the long-length imaging range, by implementing the fluoroscopy, in which a weaker dose of an X-ray than that on the long-length imaging to generate the long-length image is irradiated to a subject M, is implemented at each and every location in the long-length imaging range; and an image connection unit 10b that generates a long-length image by connecting a plurality of X-ray images obtained by the FPD 3. The dose operation unit 10a corresponds to the data conversion means and weighting factor setting means of the present invention and the image connection unit 10b corresponds to the image connection means of the present invention. In addition, the X-ray tube 2 and the dose operation unit 10a correspond to the data acquisition means of the present invention. The inventor sets forth the specific functions of the dose operation unit 10a and the image connection element 10b referring to FIG. 4, FIG. 5 later.

The controller 11 comprises a central processing unit (CPU) and so forth and the memory element 12 comprises memory media typically including a ROM (read-only memory), a RAM (random-access memory) and so forth. In addition, the input element 13 comprises a pointing device represented by a mouse, a keyboard, a joy stick, a trackball and a touch panel and so forth. The X-ray imaging apparatus is operable to implement an X-ray imaging of the subject M by that the FPD 3 detects X-rays that transmit through the subject M and then that the image processing element 10 executes the image processing based on the detected X-rays to generate the X-ray image.

Figure 4:
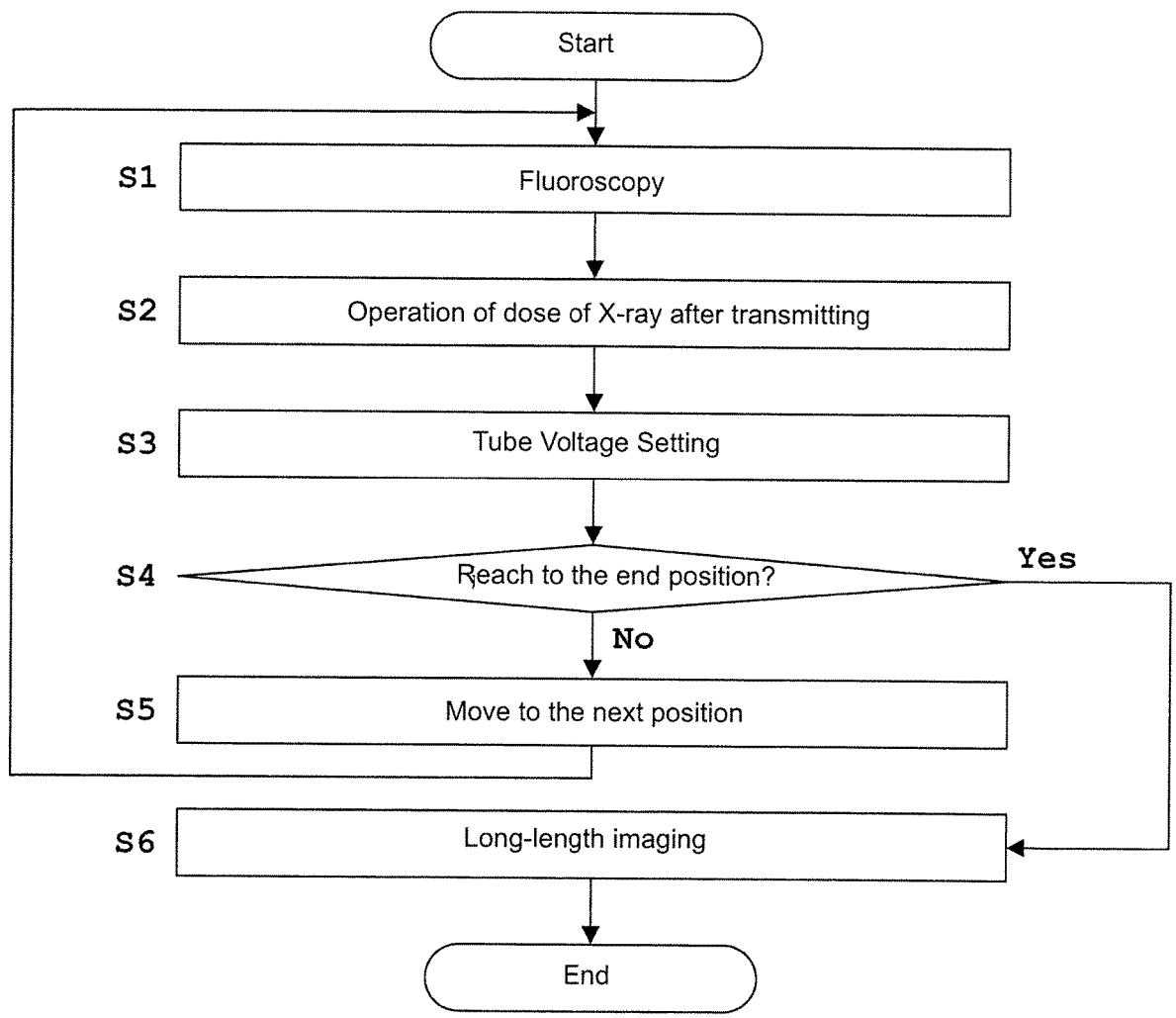
FIG. 4 is a flow-chart illustrating the flow of a fluoroscopy and a long-length imaging according to the aspect of the Embodiment.
Figure 5A:
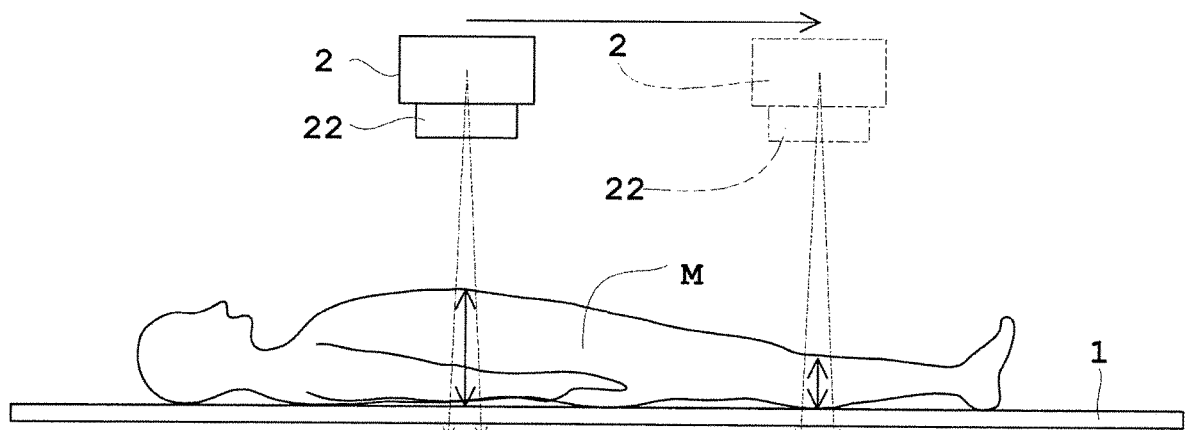
FIGS. 5A, 5B are schematic views illustrating the X-ray dose relative to the height of the subject (body thickness) at each location in the long-length imaging range after transmitting and setting of the tube voltage based on such dose.
Figure 5B:
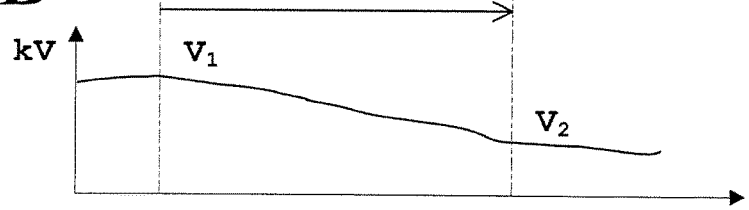

Next, the inventor sets forth the specific functions of the dose operation unit 10a and the image connection element 10b, and a specific setting and operation of the controller 11 referring to FIG. 4, FIGS. 5A, 5B. FIG. 4 is a flow-chart illustrating the flow of a fluoroscopy and a long-length imaging according to the aspect of the Embodiment, and FIGS. 5A, 5B are schematic views illustrating the X-ray dose relative to the height of the subject (body thickness) at each location in the long-length imaging range after transmitting and setting of the tube voltage based on such dose. In addition, the inventor sets forth as the long-length imaging range is already specified relative to the flow chart of FIG. 4.

(Step S1) Fluoroscopy

First, the fluoroscopy, in which an X-ray having a weaker dose than the dose on the long-length imaging to generate the long-length image is irradiated from the X-ray tube 2 (referring to FIG. 1-FIG. 3) toward the subject M is implemented. The FPD 3 (referring to FIG. 1-FIG. 3) detects the X-ray that transmits the subject M and outputs the X-ray detection signal, and then A/D converter 9 (referring to FIG. 3) digitizes and sends the X-ray detection signal to the image processing element 10 (referring to FIG. 3). In addition, the fluoroscopic image of the subject can be generated based on such digitized X-ray detection signals. Specifically, the image processing element 10 executes the processing on the digitized X-ray detection signal and outputs pixel values corresponding to the X-ray detection signals. The fluoroscopic image of the subject M projected on the detection surface of the FPD 3 by respectively aligning each pixel value every detection element of the FPD 3. Accordingly, the fluoroscopic image of the subject M is generated.

(Step S2) Operation of the X-ray Dose After Transmitting

The digitized X-ray detection signal is proportional to the X-ray dose that reaches to the FPD 3 (i.e., X-ray dose after transmitting), so that the dose operation element 10a obtains the X-ray dose after transmitting as the data relative to the height of the subject M based on the digitized X-ray detection signal. The dose is indicated as D1, . . . in FIG. 5. In addition, once the dose D1 is obtained, the fluoroscopic image is unnecessary, but such fluoroscopic image can be stored in the memory element 12 (referring to FIG. 3).

(Step 3) Setting Tube Voltages

The controller 11 (referring to FIG. 3) sets up the tube voltages as an X-ray imaging condition based on the data (X-ray dose after transmitting) relative to the height of the subject M obtained by the dose operation element 10a at the step S2. Specifically, referring to FIG. 5, as well as the automatic brightness control (IBS) function, the dose D1 at the location having the thick body thickness is less, so that the tube voltage (denoted by kV in FIG. 5) is set up to be high and vice versa, the dose D2 at the location having the thin body thickness is high, so that the tube voltage is set up to be low (refer to V2). The value of the tube voltage set up by the controller 11 is sent to the high-voltage generator 4 (referring to FIG. 3) and the high-voltage generator 4 controls the X-ray tube 2 to generate the tube voltage from the X-ray tube 2 according to the receiving tube voltage value. In such way, the tube voltage is set up so that the X-ray doses that transmit the subject M coincide with each other at each location when the long-length imaging is implemented at the step S6 set forth later.

In such way, the X-ray dose after transmitting depending on the body thickness is just needed to obtain the data relative to the height of the subject M, so that it is not absolutely essential to accurately get the body thickness. Therefore, according to the aspect of the Embodiment, the X-ray dose that transmits the subject M (i.e., X-ray dose after transmitting) is the data relative to the height of the subject M. In addition, when the relative physical value (e.g., a ratio of doses) can be provided, the X-ray dose after transmitting is not essential to be accurate. For example, given the dose is double relative to the X-ray dose after transmitting at a certain body thickness, it is deemed that the body thickness becomes half, so that the tube voltage is set up to be low. Reversely, given the dose is half relative to the X-ray dose after transmitting at a certain body thickness, it is deemed that the body thickness becomes double, so that the tube voltage is set up to be high.

In addition, according to the aspect of the Embodiment, the function of the data conversion means, and the function of the imaging condition setting means are respectively separated by the dose operation element 10a and the controller 11, the function of the data conversion means, and the function of the imaging condition setting means can be implemented by e.g., the same controller 11. In addition, a photo-timer (not shown in FIG.) has the function of the data conversion means and the photo-timer can measure the X-ray dose after transmitting.

(Step S4) Reach to the End Location?

After the controller 11 sets up the imaging condition (tube voltage) at the step S3, when the flow has attained the end location, it is deemed that the fluoroscopy attains the end location of the long-length imaging range and the step skips to the step S6. When the flow has not attained the end location, it is deemed that the fluoroscopy is not over and the step proceeds to the next step S5.

(Step S5) Moving to the Next Location

At the step S4, the flow has not attained the end location, the X-ray tube 2 is moved to the next location by that the support column driving mechanism (referring to FIG. 3) moves the X-ray tube along with the support column 21 (referring to FIG. 1-FIG. 3) in the body axis direction to implement the fluoroscopy at the next location. The FPD 3 is also moved in synchronism with the X-ray tube 2 in the body axis direction. Each location at which the fluoroscopy is implemented coincides with the location at which the long-length imaging is implemented (i.e., each location in the long-length imaging). Following moving the X-ray tube 2 to the next location, the step returns to the step S1 and the steps S1-S5 are repeated. In such way, the fluoroscopy, in which a weaker dose of an X-ray than on the long-length imaging is irradiated to a subject M from the X-ray tube 2, is implemented at each location relative to the long-length imaging range. Then, the dose operation element 10a obtains the dose D1, . . . , as the data relative to the height of the subject M at each location in the long-length imaging range based on the result of the fluoroscopy. In addition, the controller 11 sets up the tube voltage as the imaging condition based on the data (dose D1, . . . ), which is obtained by irradiating from the X-ray tube 2 that is moved by the support column driving mechanism 5, relative to the height of the subject M at each location in the long-length imaging range.

(Step S6) Long-Length Imaging

The X-ray tube 2 irradiates an X-ray toward the subject M based on the imaging condition (tube voltage) that the controller 11 sets up at the step S3. The FPD 3 detects the X-ray that transmits the subject M and outputs the X-ray detection signal as well as the fluoroscopy at the step S1, and then A/D converter 9 (referring to FIG. 3) sends the X-ray detection signal following digitization to the image processing element 10 (referring to FIG. 3). The X-ray image of the subject M projected on the detection surface of the FPD 3 is generated by aligning each pixel value, on which the image processing element 10 executes a variety of processings, every detection element of the FPD 3. The FPD 3 obtains the X-ray image thereby. As well as at the step S5, the X-ray images are respectively obtained at each location in the long-length imaging range while moving the X-ray tube 2 in the body axis direction. In such way, the image connection element 10b (referring to FIG. 3) connects a plurality of X-ray images acquired by the FPD 3 to generate a long-length image, In addition, the subject M for the fluoroscopy is preferably the same subject for the long-length imaging. Accordingly, it is preferable that the long-length imaging at the step S6 is implemented right after the step S1-S5. Needless to say, the other subject having the same size as the size of the subject M, which is the target of the long-length imaging, can be subject to the fluoroscopy, but the location of organs and bones are different from an individual to an individual even having the same size, so that it is preferable that the same subject M as the subject for the long-length imaging is subject to the fluoroscopy. The imaging condition (here, tube voltage) can be further adequately set up by implementing the fluoroscopy for the same subject M as the subject for the long-length imaging.

The X-ray imaging apparatus according to the aspect of the present Embodiment comprises a data acquisition means (X-ray tube 2 and dose operation element 10a) that acquires each of data (X-ray dose that transmits the subject according to the present Embodiment) relative to the height of the subject at each location relative to a long-length imaging range with each other. In addition, the X-ray imaging apparatus according to the aspect of the present invention further comprises an imaging condition setting means (controller 11 according to the present Embodiment) that sets up an X-ray imaging condition so that doses of X-rays that transmit the subject coincide with each other at each location based on data relative to the height of the subject at each location in the long-length imaging range that are acquired using the data acquisition means (X-ray tube 2 and dose operation element 10a). The data acquisition means (X-ray tube and dose operation element 10a) that acquires each of data relative to the height of the subject every location relative to the long-length imaging range with each other prior to the long-length imaging. The imaging condition setting means (controller 11) that sets up an X-ray imaging condition so that doses of X-rays that transmit the subject coincide with each other at each location based on data (X-ray dose that transmits the subject) relative to the height of the subject at each location in the long-length imaging range, and implements the long-length imaging, so that the imaging condition (tube voltage) relative to the long-length imaging in the region in which the height (body thickness) of the subject is different each other can be set up appropriately.

The X-ray imaging apparatus according to the aspect of the present Embodiment comprises an electromagnetic wave irradiation means (X-ray tube 2 according to the aspect of the Embodiment) that irradiates an electromagnetic wave (X-ray according to the aspect of the Embodiment) toward the subject so that the electromagnetic wave is incident into the each location in the long-length imaging range set forth above; and a data conversion means (dose operation element 10a according to the aspect of the Embodiment) that converts a dose of such electromagnetic wave, which is irradiated from the electromagnetic wave irradiation means (X-ray tube 2) to the data (X-ray dose that transmits the subject) relative to the height of the subject at each location relative to a long-length imaging range. The electromagnetic wave irradiation means (X-ray tube 2) irradiates the electromagnetic wave (X-ray) toward the subject M so that the electromagnetic wave is incident into each location relative to the long-length imaging range prior to the long-length imaging. The data conversion means (dose operation element 10a) converts the electromagnetic wave, which is irradiated from the electromagnetic wave irradiation means, to the data (X-ray dose that transmits the subject M) relative to the height of the subject at each location in the long-length imaging range; and the imaging condition setting means (controller 11) sets up an X-ray imaging condition so that doses of X-rays that transmit the subject coincide with each other at each location based on data relative to the height of the subject at each location in the long-length imaging range, and implements the long-length imaging, so that the imaging condition (tube voltage) relative to the long-length imaging in the region in which the height (body thickness) of the subject M is different each other can be set up appropriately.

According to the aspect of the present Embodiment, one example of the electromagnetic wave that is irradiated as set forth above (irradiated prior to the long-length imaging) is an X-ray. In such case, the fluoroscopy, in which a weaker dose of an X-ray than on the long-length imaging to generate the long-length image is irradiated to the subject M from the electromagnetic wave irradiation means (X-ray tube 2), is implemented at each location relative to the long-length imaging range, and based on the results of the fluoroscopy, the data conversion means (dose operation element 10a) converts the results to the data (dose that transmits the subject M) related to the height of the subject at each and every location in the long-length imaging range. The fluoroscopy, in which a weaker dose of the X-ray than on the long-length imaging to generate the long-length image is irradiated to the subject M from the electromagnetic wave irradiation means (X-ray tube 2), is implemented at each location relative to the long-length imaging range prior to the long-length imaging. In such way, every time when the fluoroscopy is implemented at each location relative to the long-length imaging range, the data conversion means (dose operation element 10a) converts the results to the data (dose that transmits the subject M) related to the height of the subject M at each location in the long-length imaging range based on the results of the fluoroscopy prior to the long-length imaging. The imaging condition setting means that sets up an X-ray imaging condition so that doses of X-rays that transmit the subject M coincide with each other at each location based on data (X-ray dose that transmits the subject) relative to the height of the subject M at each location in the long-length imaging range, and implements the long-length imaging, so that the imaging condition (tube voltage) relative to the long-length imaging in the region in which the height (body thickness) of the subject M is different each other can be set up appropriately.

According to the aspect of the present Embodiment, it is preferable that the X-ray irradiation means (X-ray tube 2 according to the aspect of the present Embodiment) is the electromagnetic wave irradiation means as well when the electromagnetic wave is an X-ray. Accordingly, the number of the component parts of the apparatus can be cut.

In addition, according to the aspect of the present Embodiment, when the electromagnetic wave is the X-ray, the data relative to the height of the subject at each and every location in the long-length imaging range is the dose of the X-ray that transmits the subject M. As set forth above in the case of that the automatic brightness control (IBS) function as set forth above is equipped, when the thick subject M is subject to the fluoroscopy, the X-ray dose that reaches to the X-ray detector (X-ray detection means) is less, so that the tube voltage is increased to prevent such incident, and vice versa, when the thin subject M is subject to imaging, the X-ray dose that reaches to the FPD 3 is high, so that the tube voltage is decreased to prevent such incident. As results, the X-ray dose that reaches to the FPD 3 can be uniformed even when the height (body thickness) of the subject M is different in the long-length imaging range, so that the brightness (pixel value) can be appropriately adjusted.

In addition, according to the aspect of the present Embodiment, the X-ray irradiation means (X-ray tube 2) relatively moves so that the X-ray moves relatively to be incident relative to the subject M in the body axis direction by moving the X-ray tube 2 relative to the subject M while the subject M is fixed. In such way, the image connection means (image connection element 10b according to the aspect of the present Embodiment) generates the long-length image by connecting a plurality of X-ray images that are obtained by the X-ray detection means (FPD 3, flat panel type X-ray detector, according to the aspect of the present Embodiment) while the X-ray tube is moving relative to the subject M.

The present invention is not limited to the aspect of the Embodiment set forth above and further another alternative Embodiment can be implemented set forth below.

(1) The long-length imaging may be operable in the horizontal posture (recumbent posture), may be operable in the upright posture and may be operable in the tilting posture.

(2) According to the aspect of the above Embodiment, the inventor sets forth a flat panel type detection (FPD) as an example of the X-ray detection means, but the present invention is not limited thereto as long as the X-ray detection means, such as the image intensifier, is ordinarily used.

(3) According to the aspect of the above Embodiment, the X-ray irradiation means for the long-length imaging is a tube-bulb such as an X-ray tube, the present invention is not limited thereto. The present invention is not limited thereto as long as the X-ray irradiation means is ordinarily used.

(4) According to the aspect of the above Embodiment, the inventor sets forth a slot-imaging that generates a long-length image by connecting X-ray images, which are acquired by squeezing the radiated visual field as like as a slit while adjusting the open-degree of the X-ray by a collimator, in the body axis direction, but it is not necessary that the present invention is limited thereto. The present invention can be applied to the long-length imaging that generates a long-length image by connecting the X-ray images having the same size as the size of the X-ray detection means, wherein the X-rays are irradiated to the entire surface of the X-ray detection means represented by e.g., the flat panel type detector (FPD) and so forth without squeezing the radiated visual field (5) According to the aspect of the above Embodiment, the X-ray irradiation means or the electromagnetic wave irradiation means (X-ray tube 2 according to the aspect of the Embodiment) relatively moves relative to the subject M so that the X-ray moves relatively to be incident relative to the subject in the body axis direction by moving the X-ray or the electromagnetic wave (X-ray according to the aspect of the Embodiment) relative to the subject M while the subject M is fixed, but it is not necessary that the present invention is limited to such moving aspect. Reversely, while the X-ray irradiation means or the electromagnetic wave irradiation means are fixed, the table loading the subject moves; or while the X-ray irradiation means or the electromagnetic wave irradiation means are moving, the table moves at the same time; so that the X-ray or the electromagnetic wave (X-ray) can be relatively moved to be incident relative to the subject in the body axis direction by relatively moving the X-ray irradiation means or the electromagnetic wave irradiation means.

(6) According to the aspect of the above Embodiment, the X-ray irradiation means or the electromagnetic wave irradiation means (X-ray tube 2 according to the aspect of the Embodiment) relatively moves relative to the subject so that the X-ray moves relatively to be incident relative to the subject in the body axis direction by moving the X-ray or the electromagnetic wave (X-ray according to the aspect of the Embodiment) relative to the subject M while the subject M is fixed, but it is not necessary that the present invention is limited to such moving aspect. For example, under the state in which the X-ray tube is fixed, the X-ray detection means represented by e.g., the flat panel type X-ray detector (FPD) relatively moves to the position, at which the X-ray detection means detects the X-ray while tilting the X-ray tube by controlling the face thereof; so that the X-ray tube can be relatively moved, by which the X-ray relatively moves in the body axis direction relative to the subject to be incident.

(7) According to the aspect of the Embodiment set forth above, the X-ray irradiation means (X-ray tube 2 according to the aspect of the present Embodiment) is the electromagnetic wave irradiation means in the case of that the electromagnetic wave is an X-ray, but it is not necessary that the X-ray irradiation means is the electromagnetic wave irradiation means. The X-ray irradiation means (X-ray tube 2) for the long-length imaging and the X-ray irradiation means for the fluoroscopy to implement the fluoroscopy as the electromagnetic wave irradiation means prior to the long-length imaging can be installed independently.

(8) According to the aspect of the Embodiment set forth above, the inventor sets forth the dose of the X-ray that transmits a subject (dose of the X-ray after transmitting) as the data relative to the height of the subject for example, but it is not necessary that present invention is limited to the dose of the X-ray after transmitting. For example, when the electromagnetic wave is the X-ray, the fluoroscopy is implemented by irradiating the X-ray from the side of body so that the body thickness as the data relative to the height of the subject can be directly obtained from the number of pixels of the body thickness incorporated in the fluoroscopic image and the magnification ratio thereof based on the fluoroscopic image at each location in the long-length imaging range incorporating the body thickness of the subject. In addition, the fluoroscopy is implemented by irradiating the X-ray from the same direction as the direction (right above or right under in the case of horizontal posture) for the long-length imaging, so that the body thickness as the data relative to the height of the subject can be directly obtained from the number of pixels of the body width incorporated in the fluoroscopic image, the distance (SID, source image distance) between the X-ray tube and the FPD, and the width size of the FPD and so forth based on the fluoroscopic image at each location in the long-length imaging range incorporating the body width thickness of the subject. For example, regardless the height of the table, given the fluoroscopy is the data due to half-thickness of the body of the subject, if the body width in the fluoroscopic image based on the number of pixel incorporated in the fluoroscopic image is d, the distance between the X-ray tube and the FPD is SID (known), the width size of the FPD is S (known) and the body thickness of the subject H(d) (unknown), SID/S=H(d)/2/d, i.e., H(d)=2/S×d×SID is obtained from the similarity relationship, and the body width d in the fluoroscopic image, which is obtained from the number of pixels of the body width, so that the body thickness H(d) of the subject can be obtained by substituting the body width d in the above formula.

Figure 6:
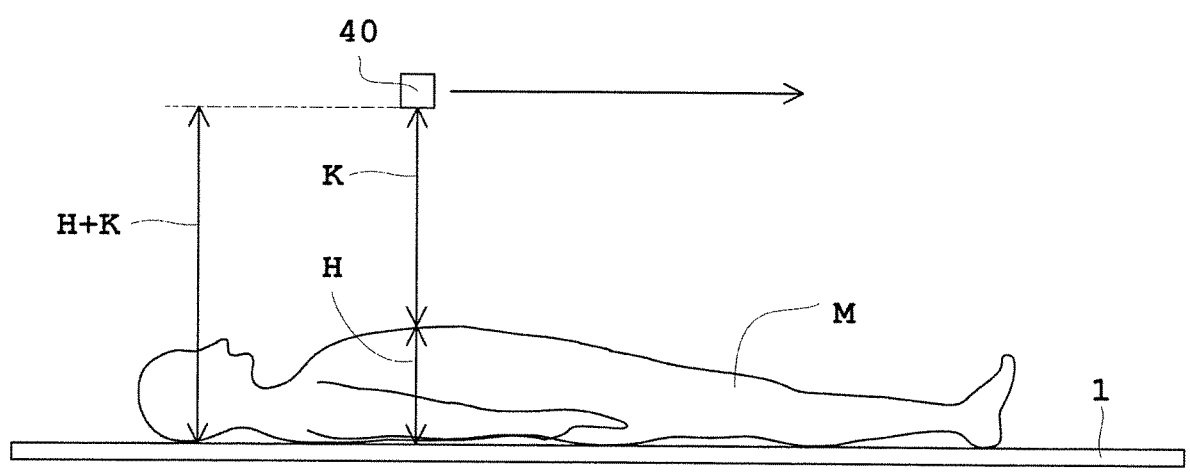
FIG. 6 is a schematic view illustrating the time when acquiring the height of the subject at each location in the long-length imaging range when an ultrasound is used.

(9) According to the aspect of the Embodiment set forth above, the electromagnetic waves (X-ray according to the aspect of the Embodiment) (irradiated prior to the long-length imaging) are respectively converted to the data (X-ray dose that transmits the subject according to the aspect of the Embodiment) relative to the height of the subject at each location in the long-length imaging range, the applied ultrasounds other than electromagnetic wave can be converted to the data relative to the height of the subject. For example, referring to FIG. 6, the body thickness can be obtained using the ultrasound. When an ultrasound irradiation mechanism 40 moves in the body axis direction, the distance between the ultrasound irradiation mechanism 40 and the body surface of the subject M is K, and each distance K at each location in the long-length imaging range is measured using the ultrasound irradiation mechanism 40. The distance (H+K) between the ultrasound irradiation mechanism 40 and the table 1 is known, and the ultrasound irradiation mechanism 40 measures each distance K at each location in the long-length imaging range, so that the body thickness H at each location of the long-length imaging range can be respectively obtained.

Figure 7A:
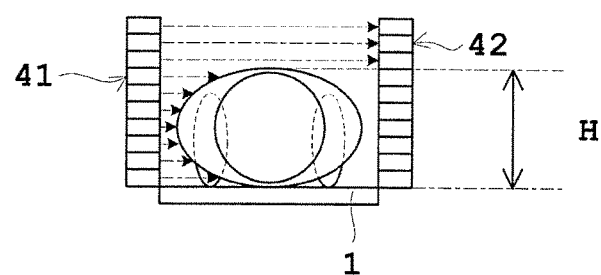
FIGS. 7A, 7B are schematic views illustrating the time when acquiring the height of the subject at each location in the long-length imaging range when a light is used.
Figure 7B:
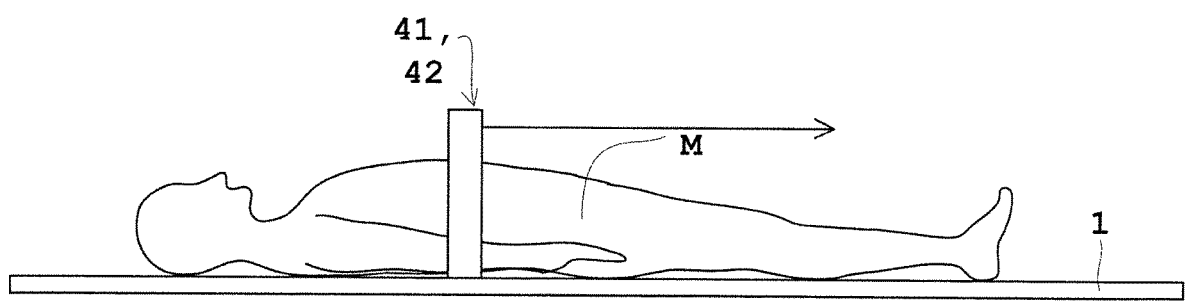

(10) According to the aspect of the Embodiment set forth above, the electromagnetic waves (irradiated prior to the long-length imaging) is X-ray, but an electromagnetic wave (e.g., light) other than an X-ray can be converted to the data relative to the height of the subject. For example, referring to FIG. 7, the body thickness can be obtained using the light. Referring to FIG. 7A, a line sensor consisting of a plurality of light emission elements 41 having at least the width of the body thickness of the subject M and a plurality of light receiving elements 42 are equipped and, referring to FIG. 7B, such light emission elements 41 and light receiving elements 42 move in the body axis direction to provide the body thickness H of the subject at each location in the long-length imaging range. Referring to FIG. 7A, when the line sensor is a transmission type, the body thickness H of the subject M at each location in the long-length imaging range can be respectively obtained based on the number of the light receiving elements that are blocked by the subject M. In addition, even not shown in FIG., when the line sensor is a reflection type sensor, a plurality of light emission elements having at least the width of the body thickness of the subject and a plurality of light receiving elements are equipped in the same side, and such light emission elements and light receiving elements move in the body axis direction to provide the body thickness H of the subject at each location in the long-length imaging range based on the number of receiving elements that are reflected from the subject.

(11) According to the aspect of the Embodiment set forth above, the tube voltage is set up as an X-ray imaging condition, an imaging condition other than the tube voltage is applicable. For example, a tube electric current or an irradiation time can be set up as such imaging condition.

Although only a few embodiments have been disclosed in detail above, other embodiments are possible, and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Those of skill would further appreciate that the various illustrative logical blocks, modules, circuits, and algorithm steps described in connection with the embodiments disclosed herein may be implemented as electronic hardware, computer software running on a specific purpose machine that is programmed to carry out the operations described in this application, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the exemplary embodiments.

A processor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein.

The steps of a method or algorithm described in connection with the embodiments disclosed herein may be embodied directly in hardware, in a software module in memory retained in and executed by a processor, using cloud computing, or in combinations. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of tangible storage medium that stores tangible, non-transitory computer based instructions. An exemplary storage medium is coupled to the processor such that the processor can read information from, and write information to, the storage medium. In the alternative, the storage medium may be integral to the processor. The processor and the storage medium may reside in reconfigurable logic of any type.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer.

The memory storage can also be rotating magnetic hard disk drives, optical disk drives, or flash memory based storage drives or other such solid state, magnetic, or optical storage devices. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media. The computer readable media can be an article comprising a machine-readable non-transitory tangible medium embodying information indicative of instructions that when performed by one or more machines result in computer implemented operations comprising the actions described throughout this specification.

The computers described herein may be any kind of computer, either general purpose, or some specific purpose computer such as a workstation. The programs may be written in C, or Java, Brew or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

Also, the inventors intend that only those claims which use the words "means for" are intended to be interpreted under 35 USC 112, sixth paragraph. Moreover, no limitations from the specification are intended to be read into any claims, unless those limitations are expressly included in the claims.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

REFERENCE OF SIGNS

2 X-ray tube
3 Flat panel type X-ray detector (FPD.)
10a Dose operation element
10b Image connection element
11 Controller
M Subject

What is claimed is:

1. An X-ray imaging method that implements an X-ray imaging, comprising:
 a long-length imaging range determining step that determines a start position and an end position of a long-length imaging range based on an image of fluoroscopy in which a weaker X-ray dose than on a long-length imaging that generates a long-length image is irradiated toward a subject from an X-ray irradiator;
 a data acquisition step that acquires a plurality of data relative to a height of the subject at a plurality of locations relative to the long-length imaging range based on a plurality of doses of X-rays at the plurality of locations relative to the long-length imaging range acquired by the fluoroscopy that are obtained by said long-length imaging range determining step;
  wherein the plurality of doses of x-rays are acquired by a dose operation element;
 an imaging condition setting step that sets up an X-ray imaging condition so that one or more doses of X-rays that transmit said subject coincide with each other at each said location based on said data relative to the height of said subject at each of the plurality of locations in said long-length imaging range that are acquired by said data acquisition step;
 an X-ray irradiation step irradiates an X-ray to said subject based on the imaging condition that is set up by said imaging condition setting step;
 an X-ray detection step including providing an X-ray detector that detects an X-ray that transmits said subject;
 an X-ray image generation step including an image processing element that generates a plurality of X-ray images at the plurality of locations relative to the long-length imaging range based on the X-rays detected by the X-ray detection step; and
 an image connection step that connects the plurality of X-ray images that are obtained by said X-ray detection step to generate a long-length image.

\* \* \* \* \*